US009796889B2

(12) United States Patent
Giardello et al.

(10) Patent No.: US 9,796,889 B2
(45) Date of Patent: Oct. 24, 2017

(54) METATHESIS-ACTIVE ADHESION AGENTS AND METHODS FOR ENHANCING POLYMER ADHESION TO SURFACES

(71) Applicant: MATERIA, INC., Pasadena, CA (US)

(72) Inventors: Michael A. Giardello, Pasadena, CA (US); Christopher M. Haar, Pasadena, CA (US); Brian Edgecombe, Anaheim, CA (US); Anthony R. Stephen, South Pasadena, CA (US); Li-Sheng Wang, Azusa, CA (US); Diana Stoianova, Monrovia, CA (US)

(73) Assignee: MATERIA, INC., Pasadena, CA (US)

( * ) Notice: Subject to any disclaimer, the term of this patent is extended or adjusted under 35 U.S.C. 154(b) by 0 days.

(21) Appl. No.: 14/926,830

(22) Filed: Oct. 29, 2015

(65) Prior Publication Data
US 2016/0186022 A1    Jun. 30, 2016

Related U.S. Application Data

(60) Division of application No. 13/838,459, filed on Mar. 15, 2013, now abandoned, which is a continuation-in-part of application No. 13/165,515, filed on Jun. 21, 2011, now Pat. No. 8,597,794, which is a continuation of application No. 12/042,236, filed on Mar. 4, 2008, now Pat. No. 7,964,320, which is a division of application No. 10/178,373, filed on Jun. 24, 2002, now Pat. No. 7,339,006, which is a division of application No. 09/497,741, filed on Feb. 4, 2000, now Pat. No. 6,409,875.

(60) Provisional application No. 60/118,864, filed on Feb. 5, 1999.

(51) Int. Cl.
| | | |
|---|---|---|
| C09J 145/00 | (2006.01) |
| C07C 265/08 | (2006.01) |
| C08F 32/08 | (2006.01) |
| C08F 263/04 | (2006.01) |
| C09J 4/00 | (2006.01) |
| C08G 61/08 | (2006.01) |
| C09J 5/00 | (2006.01) |
| C09J 165/00 | (2006.01) |

(52) U.S. Cl.
CPC ........... *C09J 145/00* (2013.01); *C07C 265/08* (2013.01); *C08F 32/08* (2013.01); *C08F 263/04* (2013.01); *C08G 61/08* (2013.01); *C09J 4/00* (2013.01); *C09J 5/00* (2013.01); *C08G 2261/142* (2013.01); *C08G 2261/144* (2013.01); *C08G 2261/3324* (2013.01); *C08G 2261/418* (2013.01); *C09J 165/00* (2013.01)

(58) Field of Classification Search
CPC ................. C09J 159/00; C07C 6/02
See application file for complete search history.

(56) References Cited

U.S. PATENT DOCUMENTS

| | | |
|---|---|---|
| 4,020,218 A | 4/1977 | Ranney et al. |
| 5,055,499 A | 10/1991 | Endo et al. |
| 5,077,414 A | 12/1991 | Arduengo, III |
| 5,096,644 A | 3/1992 | Endo et al. |
| 5,182,405 A | 1/1993 | Arduengo, III et al. |
| 5,312,940 A | 5/1994 | Grubbs et al. |
| 5,342,909 A * | 8/1994 | Grubbs ............ C07F 15/002 526/170 |
| 5,527,835 A | 6/1996 | Shustack |
| 5,710,298 A | 1/1998 | Grubbs et al. |
| 5,728,785 A | 3/1998 | Grubbs et al. |
| 5,728,839 A | 3/1998 | Herrmann et al. |
| 5,728,917 A | 3/1998 | Grubbs et al. |
| 5,750,815 A | 5/1998 | Grubbs et al. |
| 5,831,108 A | 11/1998 | Grubbs et al. |
| 5,840,238 A | 11/1998 | Setiabudi et al. |
| 5,849,851 A | 12/1998 | Grubbs et al. |
| 5,880,231 A | 3/1999 | Grubbs et al. |
| 5,932,664 A | 8/1999 | Chen et al. |
| 5,936,100 A | 8/1999 | Furstner et al. |
| 5,939,504 A | 8/1999 | Woodson, Jr. et al. |
| 5,962,703 A | 10/1999 | Moszner et al. |
| 5,969,170 A | 10/1999 | Grubbs et al. |
| 6,001,909 A | 12/1999 | Setiabudi |

(Continued)

FOREIGN PATENT DOCUMENTS

| | | |
|---|---|---|
| CA | 2242060 A1 | 1/1999 |
| EP | 0889107 A2 | 6/1998 |

(Continued)

OTHER PUBLICATIONS

Hercules343 (RD 34301, Research Disclosure, Nov. 1992).*
RD 319027, Research Disclosure, Nov. 1990, No. 319.
RD 343001, Research Disclosure, Nov. 1992, No. 343.
Herrmann et al., "Nickel(II) Complexes of N-Heterocyclic Carbenes," Organometallics 16:2209-2212 (1997).
Herrmann et al., "N-Heterocyclic Carbenes," Angew Chem. Int. Ed. Engl. 36:2162-2187 (1997).
Glander et al., "Development and Application of Highly Efficient Ruthenium-Based Catalysts for the Ring Opening Metathesis Polymerization," Macromol. Symp. 127:67-75 (1998).
Nolan, "Synthetic, Thermochemical and Catalytic Studies of Ruthenium and Rhodium Complexes," Jun. 26, 1998.
Herrmann et al., "A Novel Class of Ruthenium Catalysts for Olefin Metathesis," Abstract: 11th International Symposium On Homogenous Catalysis, University of St. Andrews, Scotland U.K. Jul. 1998.

(Continued)

*Primary Examiner* — Kuo-Liang Peng
(74) *Attorney, Agent, or Firm* — J.A. Lindeman & Co., PLLC

(57) ABSTRACT

The invention discloses an adhesion agent composition comprising at least one $C_3$-$C_{200}$ olefin compound having at least one metathesis active double bond, wherein the olefin is substituted or unsubstituted; and at least one compatibilizing functionality for interacting with a substrate surface. The substrate surface can be any surface, for example, silicate glasses, silicate minerals, metals, metal alloys, ceramics, natural stones, plastics, carbon, silicon, and semiconductors. The invention also discloses articles of manufacture utilizing these adhesion agents as well as methods for adhering a polyolefin to a substrate surface.

16 Claims, No Drawings

(56) References Cited

U.S. PATENT DOCUMENTS

| | | | |
|---|---|---|---|
| 6,020,443 | A | 2/2000 | Woodson et al. |
| 6,025,496 | A | 2/2000 | Herrmann et al. |
| 6,057,460 | A | 5/2000 | Moszner et al. |
| 6,100,323 | A | 8/2000 | Setiabudi et al. |
| 6,107,420 | A | 8/2000 | Grubbs et al. |
| 6,409,875 | B1 | 6/2002 | Giardello et al. |
| 6,525,125 | B1 | 2/2003 | Giardello et al. |
| 6,635,768 | B1 | 10/2003 | Herrmann et al. |

FOREIGN PATENT DOCUMENTS

| | | | |
|---|---|---|---|
| JP | S62-122718 | A | 6/1987 |
| JP | H02-185558 | A | 7/1990 |
| JP | H02-258787 | A | 10/1990 |
| JP | H02-270888 | A | 11/1990 |
| JP | H03-015212 | A | 1/1991 |
| JP | H07-323439 | A | 12/1995 |
| JP | H09-323911 | A | 12/1997 |
| JP | H09-323913 | A | 12/1997 |
| WO | 93/20111 | A2 | 10/1993 |
| WO | 97/14738 | A1 | 4/1997 |
| WO | 97/20865 | A1 | 6/1997 |
| WO | 97/29135 | A1 | 8/1997 |
| WO | 99/11454 | A1 | 3/1999 |
| WO | 99/51344 | A1 | 10/1999 |
| WO | 00/15339 | A1 | 3/2000 |
| WO | 00/58322 | A1 | 10/2000 |
| WO | 00/71554 | A2 | 11/2000 |

OTHER PUBLICATIONS

Herrmann et al., "A Novel Class of Ruthenium Catalysts for Olefin Metathesis," Angew. Chem. Int. Ed. 37 (18):2490-2493 (1998).
Ackermann et al., "Ruthenium Carbene Complexes with Imidazolin-2-ylidene Ligands Allow the Formation of Tetrasubstituted Cycloalkenes by RCM," Tetrahedron Letters 40:4787-4790 (1999).
Huang et al., "Influence of Sterically Demanding Carbene Ligation on Catalytic Behavior and Thermal Stability of Ruthenium Olefin Metathesis Catalysts," Organometallics 18:5375-5380 (1999).
Huang et al., "Olefin Metathesis-Active Ruthenium Complexes Bearing a Nucleophilic Carbene Ligand," JACS 121:2674-2678 (1999).
Furstner et al., "Cationic ruthenium allenylidene complexes as a new class of performing catalysts for ring closing metathesis," Chem. Commun. 1315-1316 (1998).
European Decision for EP 00 919 265.9 dated Nov. 17, 2011.
International Preliminary Examination Report for PCT/US00/03002 dated Oct. 26, 2000.
International Search Report for PCT/US00/03002 dated Jun. 13, 2000.
Supplemental European Search Report for EP 00 919 265 dated Apr. 12, 2005.
English-language abstract for JP H02-258787.
English-language abstract for Jp H02-270888.
English-language abstract for JP S62-122718.
English-language abstract for JP H03-015212.
English-language abstract for JP H07-323439.
Bateman et al., "Alkylation of Porous Silicon by Direct Reaction with Alkenes and Alkynes," Angew. Chem. Int. Ed. 37 (19):2683-2685 (1998).
Cagliostro et al., "Multifunctinal Alkoxysilanes as Water Repellents: Waterproofing Alumina Thermal Insulation with Methyldimethoxysilane," Journal of Advanced Materials 31:27-35 (1999).
Duchet et al., "Effect of the Length of Tethered Chains and the Interphase Structure on Adhesion between Glass and Polyethylene," Macromolecules 31(23):8264-8272 (1998).
Effenberger et al., "Photoactivated Preparation and Patterning of Self-Assembled Monolayers with 1-Alkenes and Aldehydes on Silicon Hydride Surfaces," Angew. Chem. Int. Ed. 37:2462-2464 (1998).
Monte et al., Kenrich Petrochemicals, Inc., "Ken-React® Reference Manual—Titanate, Zirconate, and Aluminate coupling Agents." (Bulletin KR 0395) (Summer 1993—Second Revised Edition), Table of Contents.
O'Brien et al., "Synthesis and Characterization of Ferrocenyl-Modified Mesoporous Silicates," Chem. Mater. 10:4088-4099 (1998).
Ullman, An Introduction to Ultrathin Organic Films: From Langmuir-Blodgett to Self-Assembly; Academic Press: San Diego (1991), Table of Contents.
Weck et al., "Ring-Opening Metathesis Polymerization from Surfaces," J. Am. Chem. Soc. 121:4088-4089 (1999).
Zhao et al., "Trichlorosilane Chemisorption on Surface-Modified Poly(tetrafluoroethylene)," Macromolecules 32 (3):796-800 (1999).

\* cited by examiner

METATHESIS-ACTIVE ADHESION AGENTS AND METHODS FOR ENHANCING POLYMER ADHESION TO SURFACES

CROSS REFERENCE TO RELATED APPLICATIONS

This application is a divisional of U.S. patent application Ser. No. 13/838,459 filed Mar. 15, 2013, which is a continuation-in-part of U.S. patent application Ser. No. 13/165,515 filed Jun. 21, 2011, which is a continuation of U.S. patent application Ser. No. 12/042,236 filed Mar. 4, 2008 (now U.S. Pat. No. 7,964,320 issued Jun. 21, 2011), which is a divisional of U.S. patent application Ser. No. 10/178,373 filed Jun. 24, 2002 (now U.S. Pat. No. 7,339,006 issued Mar. 4, 2008), which is a divisional of U.S. patent application Ser. No. 09/497,741 filed Feb. 4, 2000 (now U.S. Pat. No. 6,409,875 issued Jun. 25, 2002), which claims the benefit of U.S. Provisional Patent Application No. 60/118,864 filed Feb. 5, 1999, the contents of all of which are incorporated herein by reference.

FIELD OF THE INVENTION

The invention is directed generally to novel adhesion agents that enhance the adhesion of polymers to various substrate surfaces. More specifically, the invention relates to novel adhesion agents that comprise olefin compounds having a metathesis-active double-bond and to methods for enhancing the surface adhesive properties of ring opening metathesis polymerized (ROMP) polymers using such adhesion agents.

BACKGROUND OF THE INVENTION

It is advantageous in many commercial applications to have strong adhesion between polymers (e.g., plastic resin coatings) and various substrate surfaces. Polymer coatings may be used, for example, to protect underlying surfaces from environmental and atmospheric conditions. In this manner, polymer coatings are useful in increasing the durability and extending the "life" of various surfaces, including glass optical fibers and mirrors. Adhesion is particularly important in high humidity and high temperature environments, where there is an increased risk of delaminating or "peeling" a polymer coating from a surface.

Various adhesion promoters have been used in an effort to improve the adhesive strength and durability of adhesion of polymers to surfaces. Silane coupling agents have been used to improve, for example, the adhesion of polymer coatings to glass optical fibers, the consolidation of fillers and reinforcements into a polymeric resin matrix, and the water repellency of ceramics. Certain of these common silane coupling agents are described in U.S. Pat. No. 5,527,835, issued Jun. 18, 1996 to Shustack; other embodiments of this principle were elucidated by Warner et al. (WO 99/11454), Setiabudi (U.S. Pat. No. 6,001,909), and Cagliostro et al. (*Journal of Advanced Materials* 1999, 31, 27-35). Commercially available organotitanate, aluminate, and -zirconate compounds such as those offered by Kenrich Petrochemicals, Inc. are also useful for improving the adhesion and compatibility of polymers with a wide variety of mineral, metallic, inorganic, rubber, and plastic resin fillers, reinforcements, and surfaces (see, for example, (a) Monte, S. J. and Sugerman, G., Kenrich Petrochemicals, Inc., "Ken-React® Reference Manual—Titanate, Zirconate, and Aluminate Coupling Agents." (Bulletin KR 0395), 227 pages, (Summer 1993—Second Revised Edition); (b) Monte, S. J. *Rubber Technology International* '96; (c) Dawson, B. *Rubber and Plastics News*, Sep. 21, 1998; (d) Monte, S. J. *Reinforced Plastics, June* 1996 and references therein) the disclosures of each of which are incorporated herein by reference.

It is known in the art to use organo-functional silanes to promote adhesion of polymer resins to glass surfaces. Organo-functional silane coupling agents used in the prior art include amino-functional silanes, acrylamido-functional silanes, allyl-functional silanes, vinyl-functional silanes, acrylate-functional silanes, methacrylate-functional silanes, and mercapto-functional silanes. Furthermore, academic and industrial researchers have for many years been investigating a variety of methods for applying thin organic films to a myriad of surfaces (see, for example: (a) Ullman, A. *An Introduction to Ultrathin Organic Films: From Langmuir-Blodgett to Self-Assembly*; Academic Press: San Diego, 1991; (b) Weck, M.; Jackiw, J. J.; Rossi, R. R.; Weiss, P. S.; Grubbs, R. H. *J. Am. Chem. Soc.* 1999, 121, 4088-9; (c) Duchet, J.; Chapel, J.-P., Chabert, B.; Gerard, J.-F. *Macromolecules* 1998, 31, 8264-72; (d) Zhao, B.; Brittain, W. J.; Vogler, E. A. *Macromolecules* 1999, 32, 796-800; (e) Bateman, J. E.; Eagling, R. D.; Worrall, D. R.; Horrocks, B. R.; Houlton, A. *Angew. Chem. Int. Ed.* 1998, 37, 2683-5; (f) Effenberger, F.; Götz, G.; Bidlingmaier, B.; Werstein, M. *Angew. Chem. Int. Ed.* 1998, 37, 2462-4; (g) O'Brien, S.; Keates, J. M.; Barlow, S.; Drewitt, M. J.; Payne, B. R.; O'Hare, D. *Chem. Mater.* 1998, 10, 4088-99; and references therein) the disclosures of which have appeared in the open literature and are incorporated herein by reference.

Polyolefin compositions, including polydicyclopentadiene (poly-DCPD), may be prepared using catalyzed olefin metathesis reactions such as, for example, ring opening metathesis polymerization (ROMP). Such olefin metathesis reactions and suitable metathesis catalysts (e.g., ruthenium- or osmium-based catalysts) have been previously described in, for example, U.S. Pat. Nos. 5,312,940, 5,342,909, 5,728,917, 5,710,298, 5,831,108, and 6,001,909; PCT Publications WO 97/20865, WO 97/29135 and WO 99/51344; in U.S. Provisional Patent Application No. 60/142,713 filed Jul. 7, 1999 entitled "ROMP Reactions Using Imidazolidine-Based Metal Carbene Metathesis Catalysts;" and by Fürstner, Picquet, Bruneau, and Dixneuf in Chemical Communications, 1998, pages 1315-1316, the disclosures of each of which are incorporated herein by reference.

The aforementioned surface coupling agents, however, are not active in olefin ROMP reactions; rather, their efficacy as adhesion agents for ROMP polymers, such as poly-DCPD, is primarily the result of attractive London dispersion forces, also known as van der Waal's interactions, which are the weakest type of intermolecular forces. Thus, there exists a need for metathesis-active adhesion agents that provide enhanced adhesion of ROMP polyolefins to various substrate surfaces by covalently incorporating such adhesion agents into these ROMP polyolefins.

SUMMARY OF THE INVENTION

The invention relates to novel adhesion agents that comprise compounds having at least one metathesis-active double-bond. More specifically, the invention provides metathesis-active adhesion agent compositions and methods for enhancing the adhesive strength and durability of adhesion of polymers produced by metathesis to substrate surfaces.

The adhesion agents of the invention are useful for increasing the adhesion of various polyolefins to substrate surfaces including, but not limited to, silicate glasses and minerals, metals, metal alloys, ceramics, natural stones (e.g., marble and granite), plastics, carbon, silicon, and semiconductors. The adhesion agent compositions comprise olefin compounds having at least one metathesis-active double-bond, which is defined as a double bond active in olefin cross-metathesis reactions or in ring-opening metathesis reactions such as, for example, ROMP reactions.

In principle, any carbon-carbon double bond is capable of undergoing cross metathesis reactions in the presence of a suitable olefin metathesis catalyst. Similarly, any cyclic olefin is capable of undergoing ring-opening by olefin metathesis. Accordingly, for example, when contacted with resins comprising dicyclopentadiene (DCPD) or other cyclic olefin in the presence of suitable ruthenium or osmium catalysts, the metathesis-active adhesion agents of the invention are covalently incorporated into the bulk polymer backbone and thereby provide enhanced adhesion of the ring-opened polyolefin polymer to the substrate surface.

The metathesis-active adhesion agents taught in the invention comprise compounds having at least one metathesis-active double bond and at least one compatiblizing functionality capable of an attractive interaction with functional groups present at the (native or functionalized) substrate surface. Particularly preferred metathesis-active olefinic moieties include norbornenes, cyclopropenes, cyclobutenes, or other cyclic olefins. Particularly preferred compatiblizing functionalities include, for example, metal or silyl halides, ethers, and alkoxides for hydroxylated surfaces; acidic groups (e.g., carboxylic and mineral acids, boranes, alanes, and the like) for basic surfaces; basic groups (e.g., alkoxides, amines, phosphines, phosphine oxides, carboxylates, ethers, thioethers, and the like) for acidic surfaces; amphoteric groups such as alcohols; and ionic groups, including ammonium, phosphonium, sulfonate, and conjugate ions of the weak acids and bases mentioned above, for ionic surfaces.

One aspect of the invention is a novel metathesis-active adhesion agent. Another aspect of the invention is a method for enhancing adhesion of polyolefins to substrate surfaces through the use of such adhesion agents. A further aspect of the invention is an article of manufacture, such as a molded part, comprising a polyolefin adhered to a substrate surface using a metathesis-active adhesion agent of the invention. These and other aspects of the invention will be apparent to one skilled in the art in light of the following detailed description of the preferred embodiments.

DETAILED DESCRIPTION OF THE PREFERRED EMBODIMENTS

The invention is directed to adhesion agents comprising olefin compounds having at least one metathesis-active double-bond. In certain preferred embodiments, the invention provides metathesis-active adhesion agent compositions, as well as methods for enhancing the adhesive strength and durability of adhesion of polymers produced by metathesis to substrate surfaces.

The metathesis-active adhesion agent compositions of the invention comprise compounds having at least one metathesis-active double-bond and at least one compatiblizing functionality capable of interacting attractively with functional groups present at the substrate surface. These adhesion agents provide enhanced adhesion of a ring-opened polyolefin polymer to an underlying substrate surface through the covalent incorporation of the metathesis-active moiety into the bulk ROMP polymer while the compatiblizing functionality remains firmly bound to the substrate surface. In preferred embodiments, the adhesion agents, when contacted with resins comprising dicyclopentadiene (DCPD) or other cyclic olefin in the presence of a suitable ruthenium or osmium catalyst, provide enhanced adhesion of the polyolefin polymer to the substrate surface.

In certain embodiments, the metathesis-active adhesion agents of the invention contain olefinic groups having metathesis-active double-bonds, thereby providing complementary functionality between the bulk polyolefin and the underlying substrate surface. Metathesis-active olefinic moieties include any terminal or internal, mono-, di-, or trisubstituted olefins and any cycloalkene with at least three carbon atoms. Preferably, metathesis-active olefinic moieties include mono-or disubstituted olefins and cycloolefins containing between 3 and 200 carbons. Most preferably, metathesis-active olefinic moieties include cyclic or multicyclic olefins, such as cyclopropenes, cyclobutenes, cycloheptenes, cyclooctenes, cyclooctadienes (COD), norbornenes, norbornadienes, [2.2.1]bicycloheptenes, [2.2.2]bicyclooctenes, benzocyclobutenes, cyclopentenes, cyclopentadiene oligomers including trimers, tetramers, pentamers, and the like; cyclohexenes, cyclohexenylnorbornenes, norbornene dicarboxylic anhydrides (nadic anhydrides), and substituted norbornenes including butyl norbornene, hexyl norbornene, octyl norbornene, decyl norbornene, and the like. A preferred olefin monomer for use in the invention is dicyclopentadiene (DCPD). It is also understood that such compositions include frameworks in which one or more of the carbon atoms carry substituents derived from radical fragments including halogens, pseudohalogens, alkyl, aryl, acyl, carboxyl, alkoxy, alkyl- and arylthiolate, amino, aminoalkyl, and the like, or in which one or more carbon atoms have been replaced by, for example, silicon, oxygen, sulfur, nitrogen, phosphorus, antimony, or boron. For example, the olefin may be substituted with one or more groups such as thiol, thioether, ketone, aldehyde, ester, ether, amine, amide, nitro, carboxylic acid, disulfide, carbonate, isocyanate, phosphate, phosphite, sulfate, sulfite, sulfonyl, carboiimide, carboalkoxy, carbamate, halogen, or pseudohalogen. Similarly, the olefin may be substituted with one or more groups such as $C_1$-$C_{20}$ alkyl, aryl, acyl, $C_1$-$C_{20}$ alkoxide, aryloxide, $C_3$-$C_{20}$ alkyldiketonate, aryldiketonate, $C_1$-$C_{20}$ carboxylate, arylsulfonate, $C_1$-$C_{20}$ alkylsulfonate, $C_1$-$C_{20}$ alkylthio, arylthio, $C_1$-$C_{20}$ alkylsulfonyl, and $C_1$-$C_{20}$ alkylsulfinyl, $C_1$-$C_{20}$ alkylphosphate, arylphosphate, wherein the moiety may be substituted or unsubstituted.

An exemplary aspect of the invention is that metathesis-active adhesion agents for any surface composition can be designed based on the principles taught herein. Those skilled in the art understand that the surface chemistry of a particular composition dictates the chemical and/or physical processes and reactions required to bond to said surface: For example, preferred adhesion agents for glass, silicon, or other hydroxylated surface compositions comprise compounds prepared by contacting silicon tetrachloride ($SiCl_4$) or silyl ethers with nucleophilic reagents including water, alcohols, amines, amides, phosphines, phosphides, carbanions, and alkoxides where the proportion of nucleophile to silicon in such reactions is between about 1:1 and about 3:1 parts by mole. For example, a particularly preferred adhesion agent is prepared by the reaction of $SiCl_4$ under anhydrous conditions with 0.25 equivalent of 5-norbornene-2-methanol in the presence of a proton scavenger such as triethylamine. Preferred adhesion agents for a gold surface, on the other hand, are most appropriately functionalized with thiol-containing compounds, whereas preferred agents for carbon black or titanium dioxide include titanates and zirconates. One preferred adhesion agent composition is using a norbornene where the compatibilizing functionality is of the formula $SiCl_x(ER)_{3-x}$, wherein x is in the range of 0 to 3; E may be carbon, silicon, nitrogen, phosphorus, antimony, or oxygen; and R is an alkyl or aryl and may be substituted or unsubstituted. A particularly preferred composition is where the olefin is 5-norbornene-2-methoxy, x is 0 or 3, E is oxygen, and R is methyl or ethyl.

Particularly preferred compatiblizing functionalities will therefore be chosen based upon the exact nature of the surface to be modified and include, for example, metal and silyl halides, ethers, and alkoxides for hydroxylated surfaces; substituted or unsubstituted olefins such as $C_3$-$C_{20}$ terminal olefins, or aldehydes for silicon surfaces, acidic groups (e.g., carboxylic and mineral acids, boranes, alanes, and the like) for basic surfaces; basic groups (e.g., alkoxides, amines, phosphines, phosphine oxides, carboxylates, ethers, thioethers, and the like) for acidic surfaces; amphoteric groups such as alcohols; and ionic groups, including ammonium, phosphonium, sulfonate, sulfonyls, and conjugate ions of the weak acids and bases mentioned above, for ionic surfaces; alkyl and aryl phosphine oxides; organotitante, -aluminate, and -zirconate groups have proven effective for many of the above mentioned surfaces, including fiberglass and woven glass; inorganic fillers such as carbonates, alumina trihydrate, rutile; carbon black, rubber particles, and carbon and polymeric fibers and fabrics. A particularly preferred compatibilizing functionality is a silsesquioxane.

The metathesis-active adhesion agents taught in the invention may be formulated for use with any of a variety of substrate surfaces including, but not limited to, silicate glasses, metals, metal alloys, ceramics, natural stones (e.g., marble and granite), and plastics. Substrate surface refers not only to an uncoated substrate but also to a coated surface, such as, for example a glass substrate coated with metal. It is unnecessary that the substrate surface be smooth, flat, or non-porous for the practice of the invention. For example, fibrous surfaces, woven surfaces, microparticulate surfaces, glass surfaces, ceramic surfaces, metal surfaces, carbon surfaces, and polymer surfaces may be utilized in connection with the invention, in addition to substantially large, flat, regular, or monolithic articles. The invention may also be used in conjunction with variable density polyolefin compositions that provide, for example, a substrate or coated surface. Such variable density polyolefin compositions have been described in for example, U.S. Provisional Patent Application No. 60/118,865 filed Feb. 5, 1999 and U.S. patent application Ser. No. 09/497,950, filed Feb. 4, 2000, entitled "Polyolefin Compositions Having Variable Density and Methods for their Production and Use," the contents of each of which are incorporated herein by reference.

The adhesion agents of the invention may be used to functionalize the native substrate surface prior to metathesis polymerization, or included as a component in the polymerizable resin composition, or both. In other words, the adhesion agent may be applied to or contacted with the substrate surface to functionalize (i.e., pre-treat) the surface prior to application of the resin to the surface. In this manner, the surface is provided with functional groups that are complementary to those contained in the applied polymer resin. The adhesion agent may be alternatively or additionally included in the resin formulation to be applied to the substrate, with the exception of adhesion agents containing terminal alkyl, amine, vinyl ether, thiol, and certain other functions known in the art to inhibit polymerization at higher than interfacial concentrations.

In many cases, substrates may already be widely available as pre-treated with coatings or treatments to alter their surface characteristics. For example, glass fibers or other glass substrates are commonly treated with amino- or methacryl-functionalized silanes to make them more compatible with polar resins and coatings such as epoxy resins or acrylate coatings. In such instances, it is particularly useful to have adhesion agents that can be incorporated into the resin formulation to make them more compatible with the existing coating or treatment. For example, for use with the abovementioned amino-silane treated glass substrates, olefin compounds containing isocyanate functional groups are particularly good adhesion agents. Such isocyanate-functional adhesion agents are also useful for surfaces bearing organic hydroxyl groups such as, for example, the oxidized surfaces of carbon or graphitic materials such as carbon fibers.

Isocyanate-functional adhesion agents may be conveniently obtained by reaction of an amine- or alcohol-functionalized olefin with a diisocyanate or a polyisocyanate under such conditions to obtain a significantly mono-isocyanate functionalized olefin compound. An exemplary synthesis of a particular norbornene-isocyanate adhesion agent is shown in the following scheme:

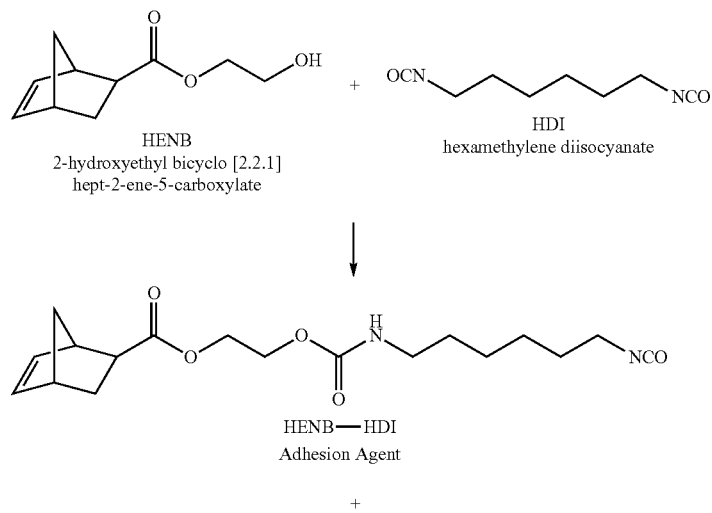

HENB
2-hydroxyethyl bicyclo [2.2.1]
hept-2-ene-5-carboxylate

HDI
hexamethylene diisocyanate

HENB—HDI
Adhesion Agent

+

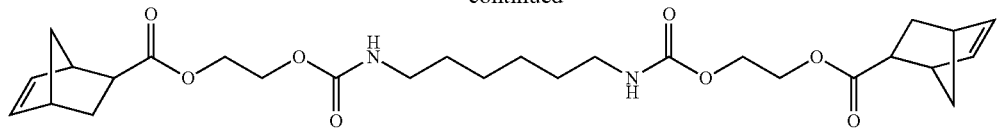

Various suitable diisocyanate or polyisocyanate compounds are commercially available due to their use in urethane resin formulations. Examples include hexamethylene diisocyanate (HDI); 5-isocyanato-1-(isocyanatomethyl)-1,3,3-trimethyl-cyclohexane (commonly known as isophorone diisocyanate or IPDI); tetramethylxylene diisocyanate (TMXDI), methylene diphenyl diisocyanate (MDI—which may comprise any mixture of its three isomers 2,2'-MDI, 2,4'-MDI, and 4,4'-MDI); 4,4'methylene bis(cyclohexyl isocyanate) (H12MDI); hexamethylene-diisocyanatetrimer (HDIt); toluene diisocyanate (TDI—which may comprise any mixture of 2,4-TDI and 2,6-TDI); and any of a number of polymeric MDIs. These may be reacted with any of a variety of functionalized olefin compounds including allyl alcohol, olelyl alcohol, and any of a number of related linear or branched enols; allyl amine, olelyl amine, and any of a number of related linear or branched enamines; norbornene alcohols such as 5-Norbornene-2-methanol (NBM) or 2-hydroxyethyl bicyclo[2.2.1]hept-2-ene-5-carboxylate (HENB); norbornene amines such as bicyclo[2.2.1]hept-2-ene-5-methylamine or 5-norbornenyl-2-methylamine (NBMA); and the like.

The reaction may be performed neat, or in solvent. Alternately, the resin that is desired to be used in the polymerization may be used as a reaction solvent. The reaction may be allowed to progress unassisted, or reaction catalysts (such as DABCO, dibutyl tin laurate, etc.) may be used. The reaction may be allowed to progress at room temperature, or at elevated temperature (>100° C.). The reaction may be performed with a 1:1 molar ratio of functionalized olefin to diisocyanate. Alternately, the reaction can be performed with an excess of functionalized olefin to reduce concentrations of unreacted diisocyanate, or an excess of diisocyanate may be used to maximize formation of the preferred mono-isocyanate adhesion promoter. As indicted in the scheme above, this method for the synthesis of the adhesion agents tend to generate reaction mixtures of mono-isocyanate olefins, di-olefins (both sites of diisocyanate reacted), and possibly unreacted diisocyanate or functionalized olefin (depending upon the initial ratios used). Even more complex mixtures will be obtained when using tri- or polyisocyanate compounds. The reaction mixture may be purified (e.g., by enriching the concentration of certain of the olefin-isocyanate species) by standard methods or used as-is without purification.

In the invention, the adhesive interaction between the native or pre-treated substrate surface and the bulk ring-opened polymer may be ionic/electrostatic, nonionic, and/or covalent in nature. The complementary functionalities provided by the adhesion agents of the invention provide "anchors" between the substrate surface and the bulk polyolefin that result in enhanced adhesive strength over silane, zirconate, titanate, aluminate and other conventional, non-metathesis-active coupling agents.

The polyolefin compositions or resins may be prepared using one or more monomers such as dicyclopentadiene, cyclopropene, cyclobutene, benzocyclobutene, cyclopentene, cyclopentadiene oligomers including trimers, tetramers, pentamers, and the like, cyclohexene, cycloheptene, cyclooctene, cycooctadiene, unsubstituted norbornenes, substituted norbornenes such as butyl norbornene, hexyl norbornene, octyl norbornene, decyl norbornene, and the like; cyclohexenylnorbornene, norbornene dicarboxylic anhydride (nadic anhydride), norbornadiene, [2.2.1]bicycloheptene, and [2.2.2]bicyclooctene. These olefin monomers may be used alone or mixed with each other in various combinations to adjust the properties of the olefin monomer composition. For example, mixtures of cyclopentadiene dimer and trimers offer a reduced melting point and yield cured olefin copolymers with increased mechanical strength and stiffness relative to pure poly-DCPD. As another example, incorporation of COD, norbornene, or alkyl norbornene comonomers tend to yield cured olefin copolymers that are relatively soft and rubbery. A preferred olefin monomer for use in the invention is dicyclopentadiene (DCPD). In addition, the resin may be substituted or unsubstituted. In polyolefin resins that are substituted, the substitution may be any moiety such as thiol, thioether, ketone, aldehyde, ester, ether, amine, amide, nitro, carboxylic acid, disulfide, carbonate, isocyanate, carboiimide, carboalkoxy, carbamate, halogen, and psuedohalogen. Similarly, the polyolefin resin may be substituted with a moiety such as $C_1$-$C_{20}$ alkyl, aryl, acyl, $C_1$-$C_{20}$ alkoxide, aryloxide, $C_3$-$C_{20}$ alkyldiketonate, aryldiketonate, $C_1$-$C_{20}$ carboxylate, arylsulfonate, $C_1$-$C_{20}$ alkylsulfonate, $C_1$-$C_{20}$ alkylthio, arylthio, $C_1$-$C_{20}$ alkylsulfonyl, and $C_1$-$C_{20}$ alkylsulfinyl, wherein the moiety may be substituted or unsubstituted.

The polyolefin compositions for use with the invention may be prepared by any standard method for the ring-opening metathesis of olefin monomers (e.g., DCPD) using a metal carbene metathesis catalyst system. Ruthenium and osmium carbene compounds have been identified as particularly effective catalysts for ROMP reactions. Exemplary olefin metathesis reactions and suitable metathesis catalysts are described in, for example, U.S. Pat. Nos. 5,312,940, 5,342,909, 5,728,917, 5,710,298, 5,831,108, and 6,001,909; PCT Publications WO 97/20865, WO 97/29135 and WO 99/51344; in U.S. Provisional Patent Application No. 60/142,713 filed Jul. 7, 1999 entitled "ROMP Reactions Using Imidazolidine-Based Metal Carbene Metathesis Catalysts;" and by Fürstner, Picquet, Bruneau, and Dixneuf in Chemical Communications, 1998, pages 1315-1316, the disclosures of each of which are incorporated herein by reference.

Any suitable metathesis catalyst may be used. Illustrative examples of suitable catalysts include ruthenium and osmium carbene catalysts as disclosed by U.S. Pat. Nos. 5,342,909; 5,312,940; 5,728,917; 5,750,815; 5,710,298, 5831,108, and 5,728,785, all of which are incorporated herein by reference. Briefly, the ruthenium and osmium carbene catalysts possess metal centers that are formally in the +2 oxidation state, have an electron count of 16, are penta-coordinated, and are of the general formula

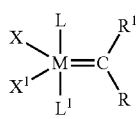

wherein:

M is ruthenium or osmium;

X and $X^1$ are each independently any anionic ligand;

L and $L^1$ are each independently any neutral electron donor ligand;

R and $R^1$ are each independently hydrogen or a substitutent selected from the group consisting of $C_1$-$C_{20}$ alkyl, $C_2$-$C_{20}$ alkenyl, $C_2$-$C_{20}$ alkynyl, aryl, $C_1$-$C_{20}$ carboxylate, $C_1$-$C_{20}$ alkoxy, $C_2$-$C_{20}$ alkenyloxy, $C_2$-$C_{20}$ alkynyloxy, aryloxy, $C_2$-$C_{20}$ alkoxycarbonyl, $C_1$-$C_{20}$ alkylthio, $C_1$-$C_{20}$ alkylsulfonyl and $C_1$-$C_{20}$ alkylsulfinyl. Optionally, each of the R or $R^1$ substituent group may be substituted with one or more moieties selected from the group consisting of $C_1$-$C_{10}$ alkyl, $C_1$-$C_{10}$ alkoxy, and aryl which in turn may each be further substituted with one or more groups selected from a halogen, a $C_1$-$C_5$ alkyl, $C_1$-$C_5$ alkoxy, and phenyl. Moreover, any of the catalyst ligands may further include one or more functional groups. Examples of suitable functional groups include but are not limited to: hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen.

In preferred embodiments of these catalysts, the R substitutent is hydrogen and the $R^1$ substitutent is selected from the group consisting $C_1$-$C_{20}$ alkyl, $C_2$-$C_{20}$ alkenyl, and aryl. In even more preferred embodiments, the $R^1$ substitutent is phenyl or vinyl, optionally substituted with one or more moieties selected from the group consisting of $C_1$-$C_5$ alkyl, $C_1$-$C_5$ alkoxy, phenyl, and a functional group. In especially preferred embodiments, $R^1$ is phenyl or vinyl substituted with one or more moieties selected from the group consisting of chloride, bromide, iodide, fluoride, —$NO_2$, —$NMe_2$, methyl, methoxy and phenyl. In the most preferred embodiments, the $R^1$ substitutent is phenyl.

In preferred embodiments of these catalysts, L and $L^1$ are each independently selected from the group consisting of phosphine, sulfonated phosphine, phosphite, phosphinite, phosphonite, arsine, stibine, ether, amine, amide, imine, sulfoxide, carboxyl, nitrosyl, pyridine, and thioether. In more preferred embodiments, L and $L^1$ are each a phosphine of the formula $PR^3R^4R^5$, where $R^3$, $R^4$, and $R^5$ are each independently aryl or $C_1$-$C_{10}$ alkyl, particularly primary alkyl, secondary alkyl or cycloalkyl. In the most preferred embodiments, L and $L^1$ ligands are each selected from the group consisting of —P(cyclohexyl)$_3$, —P(cyclopentyl)$_3$, —P(isopropyl)$_3$, and —P(phenyl)$_3$. In addition, L and $L^1$ together may comprise a bidentate ligand. Another preferred embodiment of the catalyst is where L is any neutral electron donor and $L^1$ is an imidazolidine ligand. In certain embodiments, L1 may have the general formula

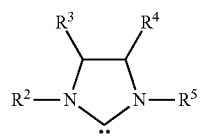

wherein:

$R^2$, $R^3$, $R^4$, and $R^5$ are each independently hydrogen or a substituent selected from the group consisting of $C_1$-$C_{20}$ alkyl, $C_2$-$C_{20}$ alkenyl, $C_2$-$C_{20}$ alkynyl, aryl, $C_1$-$C_{20}$ carboxylate, $C_1$-$C_{20}$ alkoxy, $C_2$-$C_{20}$ alkenyloxy, $C_2$-$C_{20}$ alkynyloxy, aryloxy, $C_2$-$C_{20}$ alkoxycarbonyl, $C_1$-$C_{20}$ alkylthio, $C_1$-$C_{20}$ alkylsulfonyl and $C_1$-$C_{20}$ alkylsulfinyl. $R^3$ and $R^4$ may also together form a cycloalkyl or an aryl moiety. A preferred embodiment is where $R^3$ and $R^4$ are both hydrogen or phenyl and $R^2$ and $R^5$ are each independently substituted or unsubstituted aryl. In addition, L and $L^1$ together may comprise a bidentate ligand.

In preferred embodiments of these catalysts, X and $X^1$ are each independently hydrogen, halide, or one of the following groups: $C_1$-$C_{20}$ alkyl, aryl, $C_1$-$C_{20}$ alkoxide, aryloxide, $C_3$-$C_{20}$ alkyldiketonate, aryldiketonate, $C_1$-$C_{20}$ carboxylate, arylsulfonate, $C_1$-$C_{20}$ alkylsulfonate, $C_1$-$C_{20}$ alkylthio, $C_1$-$C_{20}$ alkylsulfonyl, or $C_1$-$C_{20}$ alkylsulfinyl. Optionally, X and $X^1$ may be substituted with one or more moieties selected from the group consisting of $C_1$-$C_{10}$ alkyl, $C_1$-$C_{10}$ alkoxy, and aryl which in turn may each be further substituted with one or more groups selected from halogen, $C_1$-$C_5$ alkyl, $C_1$-$C_5$ alkoxy, and phenyl. In more preferred embodiments, X and $X^1$ are halide, benzoate, $C_1$-$C_5$ carboxylate, $C_1$-$C_5$ alkyl, phenoxy, $C_1$-$C_5$ alkoxy, $C_1$-$C_5$ alkylthio, aryl, and $C_1$-$C_5$ alkyl sulfonate. In even more preferred embodiments, X and $X^1$ are each halide, $CF_3CO_2$, $CH_3CO_2$, $CFH_2CO_2$, $(CH_3)_3CO$, $(CF_3)_2(CH_3)CO$, $(CF_3)(CH_3)_2CO$, PhO, MeO, EtO, tosylate, mesylate, or trifluoromethanesulfonate. In the most preferred embodiments, X and $X^1$ are each chloride. In addition, X and $X^1$ together may comprise a bidentate ligand.

Other additives and ingredients may be included in the resin formulations used in conjunction with the invention. Typical additives and reinforcements known in the art include, for example, antioxidants and stabilizers, flame retardants, dyes, pigments, fibers and fillers.

The invention is also directed to articles of manufacture, such as a molded part, comprising at least one polyolefin resin, at least one substrate surface, and at least one adhesion agent. Furthermore, the compositions and articles of manufacture of the invention are not limited to a single polymer-surface interface but include also multilayers and laminates containing multiple polymer-surface interfaces, i.e., multilayer laminate articles can be assembled from different layers of similar or dissimilar materials. Such articles have found use in the production of, for example, ballistic panels, "bullet proof" glass, armor, and composite structural members. An example of such a laminate structure would be layers of metal, glass, ceramic, and plastic incorporated into a single article using ROMP polyolefin compositions and metathesis-active adhesion agents as adhesives or glues between each layer.

A particular advantage of the invention is the ability to choose adhesion agents appropriate for each surface. In this way, an unlimited number of different layers, each of a different composition, can be consolidated into a single article using a single ROMP polyolefin composition as "glue" between each layer. Additionally or alternatively, more than one ROMP polyolefin can be used in such multilayer articles, as in, for example, a metal-glass-plastic article wherein the ROMP polyolefin between the metal and glass layers is stiff and strong, while that between the glass and plastic layers is soft and rubbery.

Polyolefin coatings permitted by the invention can also serve the purpose of protecting or sealing the articles to which they are applied, such as in articles and applications including, for example, water- and weatherproofing, ablative and other sacrificial coatings, lithographic or other masks, and applications wherein the seal between two surfaces must be impermeable to inert or reactive gases and liquids.

For the purposes of clarity, the specific details of the invention will be illustrated with reference to especially preferred embodiments. However, it should be appreciated that these embodiments and examples are for the purposes of illustration only and are not intended to limit the scope of the invention.

EXAMPLES

Example 1

Preparation of Norbornene-Based Adhesion Agent

A 100 ml Schlenk tube equipped with a magnetic stirring bar was charged with $SiCl_4$ (Aldrich, 50 ml of 1.0 M solution in $CH_2Cl_2$), followed by addition of 8 ml of $NEt_3$. To the stirred $SiCl_4$ solution was slowly added 6 ml of 5-norbornene-2-methanol (Aldrich), evolving heat and a copious amount of white precipitate. After the addition of the 5-norbornene-2-methanol was complete, the reaction was allowed to stir at room temperature overnight. Cannula filtration of the pale yellow reaction mixture yielded a yellow $CH_2Cl_2$ solution of the norbornene-functionalized adhesion agent.

Example 2

Adhesion of Poly-DCPD to Octyltriethoxysilane (OTES)-Treated Glass Surface

A visually clean piece of plate glass was treated by pouring 5 mL neat OTES onto the substrate and allowing the liquid to stand for 15 h. The remaining liquid was wiped away and the substrate was placed in a 40° C. oven. An activated DCPD resin at 40° C.—comprising dicyclopentadiene (BF Goodrich Ultrene 99), Ethanox 702 (Albemarle), triphenylphosphine (Strem), and metathesis catalyst dichloro(dimethylvinylmethylidine)-bis(tricyclopentylphosphine)ruthenium in the proportions 1000:30:1:1 parts by weight, respectively—was poured onto the treated glass and subjected to a cure cycle of 1 h at 40° C., 2 h at ambient, 1 h at 140° C. The hardened DCPD resin could easily be removed from the substrate by hand, indicating weak adhesion.

Example 3

Adhesion of Poly-DCPD to Metathesis-Active Allyltriethoxysilane (ATES)-Treated Glass Surface The procedure of Example 2 was repeated except 5 mL neat ATES was used to treat the glass substrate. When attempting to remove the hardened DCPD resin from the glass surface, areas of cohesive failure were observed in the glass substrate.

Example 4

Adhesion of Poly-DCPD to Norbornene-Based, Metathesis-Active Silane-Treated Glass Surface A 6"×6" panel of plate glass was cleaned with Windex™ (Johnson Wax), rinsed with acetone, and allowed to air dry. A 1 ml aliquot of the adhesion agent prepared in Example 1 was drawn into a syringe and dispensed directly onto the clean glass surface, resulting in copious evolution of gaseous HCl. The solution was allowed to dry on the glass surface, yielding a colorless, gelatinous film. The functionalized surface was then repeatedly washed with portions of toluene, acetone, and water, followed by a final rinse with acetone. The functionalized glass plate was assembled into a mold with an untreated glass panel and the mold was then heated to 40° C.

The mold was then filled with poly-DCPD resin prepared by stirring in a flask: 92 g of DCPD monomer and 2.8 g of Ethanox 702 antioxidant. This mixture was stirred and heated to 35° C., and 0.09 g of triphenylphosphine ($PPh_3$, or TPP) and 0.1 g of dimethylvinylmethylidene-bis(tricyclopentylphosphine)ruthenium dichloride catalyst were added. The resulting resin was cured at 40° C. for 30 minutes.

The mold was allowed to cool to ambient temperature for 2 hours and then was subjected to a 1 hour post-cure at 130° C. After post-cure, the untreated glass panel was easily removed while the molded plaque was still cooling. As the poly-DCPD plaque cooled and shrank, the strain introduced by adhesion of the polymer to the functionalized surface resulted in catastrophic cohesive failure within the treated glass substrate. Examination revealed that several large scallops of glass had been torn from the glass panel and remained firmly adhered to the surface of the polymer plaque.

Example 5

Adhesion of Poly-DCPD to Gold-Coated Glass Surface Treated with an Ionic, Norbornene-Based, Metathesis-Active Coupling Agent A glass slide coated on only one side with gold metal is immersed for one minute in a solution of 2-dimethylaminoethanethiol hydrochloride (Aldrich, 0.1 g in 100 ml of water), rinsed with clean water, then immersed in an ambient temperature solution of sodium 5-norbornene-2-carboxylate (0.1 g in a 1:1 (by volume) ethanol/water mixture), which is prepared by the neutralization of 5-norbornene-2-carboxylic acid with one equivalent of aqueous hydroxide ion. The temperature of the solution is then raised to 50° C. and the slide is allowed to soak at this temperature for 12 hours. After cooling to ambient temperature, the functionalized glass slide is removed from the carboxylate solution and allowed to air dry at 40° C. The functionalized glass slide is then immersed for 30-60 seconds in a freshly prepared poly-DCPD resin, prepared as in Example 2 above. The slide is removed from the poly-DCPD resin and subjected to the cure cycle as in Example 2. The poly-DCPD resin covering the unfunctionalized, non-gold coated side of the slide is easily peeled from the surface by hand, but the resin adhering to the functionalized gold-coated side requires physical scraping in order to remove the polymer from the surface.

Example 6

Poly-DCPD Safety Coating for an Untreated Glass Bottle

A poly-DCPD resin prepared as in Example 2 is maintained at 40° C. A 250 mL clear glass Boston bottle is heated to 80° C. in an oven and then dipped repeatedly into the thickening poly-DCPD resin until a persistent coating of gelled resin is apparent on the bottle. The coated bottle is allowed to cure for 1 h at 40° C., 2 h at ambient, and 1 h at 140° C. After cooling from the post cure, the cured DCPD resin on the bottle is loose and has shrunk away from the glass surface.

Example 7

Poly-DCPD Protective Coating for a Glass Bottle Treated with Norbornene-Based Metathesis-Active Coupling Agent A bottle as in Example 6 except that the exterior of the bottle is first treated as follows: A norbornene-based coupling agent is prepared from 5-norbornene-2-methanol and chlorotriethoxysilane according to the procedure in Example 1. The dry bottle is dipped into this solution, rinsed with toluene and acetone, then air dried. After post-cure and cooling, the poly-DCPD coating is firmly affixed to the bottle and must be cut or sliced to be removed.

Example 8

Addition of Cross-Metathesis Active Coupling Agent ATES to Bulk Poly-DCPD Resin

An activated poly-DCPD resin was prepared as in Example 2 with the addition of 5 parts ATES per hundred parts DCPD. This resin was then poured onto a visually clean piece of plate glass and placed in a 40° C. oven to cure. After 3 h, the poly-DCPD resin had still not cured, as determined by the tacky softness of the sample and the strong smell of unpolymerized dicyclopentadiene.

Example 9

Poly-DCPD Composite Panel with Volan-Sized Fabric

A preform consisting of 20 layers of Volan-sized 7781 E-Glass fabric was dried at 120° C. for at least 2 h, cooled to 40° C., then impregnated with a DCPD resin prepared as in Example 2. The interlaminar shear strength—often used as a test of fiber-matrix adhesion—of this composite article was found to be 2,198±84 psi as measured by the short-beam shear test (ASTM-D-2344).

Example 10

Poly-DCPD Composite Panel with Metathesis-Active ATES-Treated Volan-Sized Fabric A composite panel as in Example 9, except the oven-dried Volan-sized glass fabric was subjected to the following pre-treatment: A solution of 10 g ATES was prepared in 100 g toluene. Each ply of the preform was soaked in this solution for approximately 30 s, then stacked neatly in a second pan. The remaining solution was then poured over the stacked plies and the preform allowed to stand in this liquid for ca. 15 h. The preform was then dried in a 40° C. oven for 24 h before infusing with poly-DCPD. Interlaminar shear strength of the resulting composite as measured by the short-beam shear test (ASTM-D-2344) was found to be 2,538±45 psi.

Example 11

Poly-DCPD Composite Panel with Norbornene-Based, Metathesis-Active Silane-Treated Volan-Sized Fabric A preform was impregnated as in Example 9, but in this case, the oven dried fabric was further pre-treated as follows: A solution of the norbornene-based coupling agent prepared as in Example 1 was loaded into a 12 L round-bottom flask equipped with a Schott flange that had been dried 2 h at 120° C., then fitted with a gas inlet supplied with dry argon gas and cooled while flowing the dry gas through the vessel. The solution was diluted with ~350 mL of Aldrich Anhydrous Grade toluene, and the preform plies were soaked in this solution for approximately 5 minutes. The sizing solution was then poured off and the plies were rinsed (ca. 1 min. per aliquot) with 3×100 mL toluene followed by 3×100 mL acetone. Finally, the plies were dried in a 40° C. oven for 15 h before being stored in a sealed, polyethylene bag for several weeks before impregnation. The interlaminar shear strength of the resulting composite as measured by the short-beam shear test (ASTM-D-2344) was found to be 3,090±288 psi.

Example 12

Synthesis of HENB-HDI Adhesion Agent

HDI (hexamethylenediisocyanate or 1,6-diisocyanato-hexane) was used as received from Sigma Aldrich (98% purity). HENB (2-hydroxyethyl bicyclo[2.2.1]hept-2-ene-5-carboxylate) was prepared as described in WO 2012/174502. A 22-liter round-bottomed flask was charged with a mixture of HENB (2.70 kg, 14.8 mol), DCPD (1.0 kg), toluene (10 kg) and HDI (2.65 kg, 15.8 mol). The reaction mixture was purged with nitrogen for several minutes and then heated at 60-70° C. for three hours. The mixture was allowed to cool to room temperature and allowed to sit for 12 hours. Toluene and DCPD were then removed via vacuum distillation up to 80° C. at <1000 mtorr.

Example 13

Synthesis of HENB-TDI Adhesion Agent

TDI (80% tolylene-2,4-diisocyanate/20% tolylene-2,6-diisocyanate) was used as-received from Sigma Aldrich. A 1-liter round-bottomed flask was charged with a mixture of HENB (90 g, 0.5 mol), DCPD (0.5 kg), and TDI (98 g). The reaction mixture was purged with nitrogen and allowed to stir at room temperature (20-25° C.) for 16 hours. DCPD and residual TDI were then removed via vacuum distillation up to 80° C. at <100 mtorr.

Example 14

Synthesis of NBM-TDI Adhesion Agent

NBM (5-Norbornene-2-methanol) was used as received from Sigma Aldrich. 2,4-TDI (98% tolylene-2,4-diisocyanate) was used as-received from Sigma Aldrich. A 50-mL round-bottomed flask was charged with a mixture of NBM (15 g, 0.08 mol), DCPD (25 g), and 2,4-TDI (13 g, 0.08 mol). The reaction mixture was purged with argon and allowed to stir at room temperature (20-25° C.) for 16 hours. The resulting mixture was used without further purification.

Example 15

Synthesis of HENB-TMXDI Adhesion Agent

TMXDI (meta-tetramethylxylylene diisocyanate) was used as received from Cytec. Following the general procedure of Example 14, a mixture of HENB and TMXDI was allowed to stir at 60° C. for 72 hours in 25 g of toluene. Toluene was then removed via vacuum distillation.

Example 16

Synthesis of NBM-TMXDI Adhesion Agent

Following the general procedure of Example 14, a mixture of NBM and TMXDI was allowed to stir at 60° C. for 24 hours in 25 g of toluene. Toluene was then removed via vacuum distillation.

Example 17

Synthesis of HENB-IPDI Adhesion Agent

Following the general procedure of Example 14, a mixture of HENB and IPDI (isophorone diisocyante) was allowed to stir at 60° C. for 72 hours in 25 g of toluene. Toluene was then removed via vacuum distillation.

Example 18

Synthesis of NBM-IPDI Adhesion Agent

Following the general procedure of Example 14, a mixture of NBM and IPDI was allowed to stir at 60° C. for 24 hours in 25 g of toluene. Toluene was then removed via vacuum distillation.

Example 19

Synthesis of NBMA-HDI Adhesion Agent

NBMA (bicyclo[2.2.1]hept-2-ene-5-methylamine or 5-norbornenyl-2-methylamine) was prepared by literature methods (Tetrahedron Letters, 2008, 48, 4553). A 250-mL round-bottomed flask was charged with a mixture of toluene (140 g) and HDI (30 g, 0.178 mol). NBMA (20 g, 0.162 mol) was added dropwise over 1.5 hours and the resulting mixture was stirred for four hours at room temperature. The mixture was then filtered and the toluene was removed via vacuum distillation.

Example 20

Synthesis of HENB-HDIt Adhesion Agent

HDIt (hexamethylene diisocyanate trimer) was used as received from Bayer Material Science (Desmodur® N3300A). A 100 mL round-bottom flask was charged with HENB (6.6 g 0.036 mol), HDIt (18.4 g, 0.036 mol), and 25 g of DCPD. The vessel was purged with Argon and allowed to stir at 60° C. for 64 hours. The product was used without further purification as a solution in DCPD.

Example 21

Synthesis of 9-Decenol-HDIt Adhesion Agent

Following the general procedure of Example 14, a mixture of 9-decenol and HDIt was allowed to stir at 60° C. for 24 hours in 25 g of toluene. Toluene was then removed via vacuum distillation.

Example 22

Synthesis of 3-Hexenol-HDIt Adhesion Agent

Following the general procedure of Example 14, a mixture of 3-hexenol and HDIt was allowed to stir at 60° C. for 24 hours in 25 g of toluene. Toluene was then removed via vacuum distillation.

Examples 23-34

Poly-DCPD Composite Panels with Various Isocyanate Adhesion Agents

Preforms comprising layers of aminosilane-treated glass fabric (BGF 7781-497A) were impregnated with a DCPD resin formulation containing 20-25% tricyclopenta-diene and further comprising 2 phr Ethanox® 4702 antioxidant and 20 ppm cumyl hydroperoxide (CHP) inhibitor, catalyzed by the addition of [1,3-bis-(2,4,6-trimethylphenyl)-2-imidazolidinylidene]dichloro(3-methyl-2-butenylidene)(tricyclohexylphosphine)ruthenium (II), referred to hereinafter as C827, (monomer to catalyst ratio 60,000:1) in a suspension of mineral oil, and comprising the adhesion agents of Examples 12-21 as indicated in Table 1. The resulting composite laminates generally had a fiber volume around 50%. The interlaminar shear strength (ILSS)—often used as a test of fiber-matrix adhesion—of these composite articles were measured by the short-beam shear (SBS) test (ASTM-D-2344).

TABLE 1

Composite Sample Results for Examples 23-34

| Example | Adhesion Agent | Agent Amount (phr) | Fiber Volume (%) | ILSS (psi) |
| --- | --- | --- | --- | --- |
| 23 | none | — | 49 | 3,342 |
| 24 | HENB-HDI | 1 | 50 | 6,862 |
| 25 | HENB-TDI | 1 | 55 | 6,802 |
| 26 | NBM-TDI | 1 | 51 | 6,504 |
| 27 | HENB-TMXDI | 2 | 50 | 6,696 |
| 28 | NBM-TMXDI | 2 | 46 | 6,762 |
| 29 | HENB-IPDI | 2 | 53 | 6,598 |
| 30 | NB-M-IPDI | 2 | 51 | 6,487 |
| 31 | NBNA-HDI | 1 | 51 | 6,640 |
| 32 | HENB-HDIt | 2 | 46 | 7,024 |
| 33 | 9-Decenol-HDIt | 2 | 51 | 7,631 |
| 34 | 3-Hexenol-HDIt | 2 | 53 | 7,338 |

Examples 35-41

Performance of Isocyanate Adhesion Agents with Various Substrate Finishes

Preforms comprising layers of glass fabrics (Hexcel 7781-F12) treated with various silane finishes as indicated in Table 2 were impregnated with a DCPD resin formulation containing 20-25% tricyclopentadiene and further comprising 2 phr Ethanox® 4702 antioxidant and 20 ppm CHP inhibitor, catalyzed by the addition of C827 (monomer to catalyst ratio 60,000:1) in a suspension of mineral oil, and comprising 2 phr of the HENB-HDI adhesion agent of Example 12. The resulting composite laminates generally had a fiber volume around 50%. The ILSS of these composite articles were measured by the short-beam shear (SBS) test (ASTM-D-2344).

TABLE 2

Composite Sample Results for Examples 35-41

| Example | Finish Type | Fiber Vol. (%) | ILSS (psi) |
|---|---|---|---|
| 35 | none | 49.4 | 2,178 |
| 36 | 3-aminopropyltriethoxysilane (Gelest) | 49.9 | 7,057 |
| 37 | methacryloxypropyltrimethoxysilane (Gelest) | 49.9 | 4,185 |
| 38 | 50% 3-aminopropyltriethoxysilane 50% methacryloxypropyltrimethoxysilane | 52.0 | 6,661 |
| 39 | Ureidopropyltrimethoxysilane (Gelest) | 52.8 | 4,616 |
| 40 | N-(2-aminoethyl)-3-aminopropyl-triethoxysilane (Gelest) | 53.4 | 7,431 |
| 41 | 3-(N-styrylmethyl-2-aminoethylamino)propyl-trimethoxysilane hydrochloride (Gelest) | 46.4 | 7,357 |

Examples 42-48

Performance of Isocyanate Adhesion Agents as a Function of Loading

Preforms comprising layers of aminosilane-treated glass fabric (BGF 7781-497A) were impregnated with a DCPD resin formulation containing 20-25% tricyclopenta-diene and further comprising 2 phr Ethanox® 4702 antioxidant and 20 ppm CHP inhibitor, catalyzed by the addition of C827 (monomer to catalyst ratio 60,000:1) in a suspension of mineral oil, and comprising various amounts of the HENB-HDI adhesion agent of Example 12 as indicated in Table 3. The resulting composite laminates generally had a fiber volume around 50%. The ILSS of these composite articles were measured by the short-beam shear (SBS) test (ASTM-D-2344).

TABLE 3

Composite Sample Results for Examples 38-44

| Example | HENB-HDI Amount (phr) | Fiber Volume (%) | ILSS (psi) |
|---|---|---|---|
| 42 | 0 | 49.4 | 3,342 |
| 43 | 2.0 | 51.4 | 7,316 |
| 44 | 1.0 | 50.2 | 7,139 |
| 45 | 0.50 | 53.5 | 7,218 |
| 46 | 0.25 | 45.4 | 7,040 |
| 47 | 0.10 | 47.6 | 7,131 |
| 48 | 0.05 | 46.6 | 6,812 |

Example 49

Poly-DCPD/Carbon Composite with HENB-HDI Adhesion Agent

Preforms comprising layers of solvent-washed (toluene and acetone) and dried uni-directional carbon fiber fabric (Zoltek PX35UD0500-1230) were impregnated with a DCPD resin formulation containing 22% tricyclopentadiene and further comprising 2 phr Ethanox® 4702 antioxidant, 10 ppm CHP inhibitor, 3 phr of the HENB-HDI adhesion agent of Example 12, and catalyzed by the addition of C827 (monomer to catalyst ratio 60,000:1) in a suspension of mineral oil. The resulting composite laminate had a fiber volume of 52% and exhibited the following mechanical properties:
Flexural Strength (ASTM-D-790): 140 ksi
Flexural Modulus (ASTM-D-790): 13,100 ksi
ILSS (ASTM-D-2344): 8,400 psi

What is claimed is:

1. A method for adhering a polyolefin resin to a substrate surface comprising:
contacting a polyolefin resin with an adhesion agent in the presence of a metal carbene metathesis catalyst to form a resin/agent mixture, the adhesion agent comprising at least one $C_3$-$C_{200}$ olefin compound having at least one metathesis active double bond, wherein the olefin is substituted or unsubstituted, and at least one compatibilizing functionality for interacting with the substrate surface;
and applying the mixture to the substrate surface, wherein the substrate surface comprises amino functional groups.

2. The method according to claim 1 wherein the substrate surface comprises organic hydroxyl groups.

3. The method of claim 1 wherein the polyolefin resin is prepared from one or more monomers selected from the group consisting of cyclopropenes, cyclobutenes, benzocyclobutenes, cyclopentenes, cyclopentadiene oligomers, cyclohexenes, cycloheptenes, cyclooctenes, cycooctadienes, norbornenes, norbornadienes, [2.2.1] bicycloheptenes, [2.2.2] bicyclooctenes, cyclohexenylnorbornenes, and norbornene dicarboxylic anhydrides; and wherein the resin is substituted or unsubstituted.

4. The method of claim 1 wherein the polyolefin resin is prepared via a ring opening metathesis polymerization of a cyclic olefin.

5. The method of claim 1 wherein the polyolefin resin is poly-DCPD.

6. The method of claim 1 wherein the polyolefin resin is substituted with a moiety selected from the group consisting of $C_1$-$C_{20}$ alkyl, aryl, acyl, $C_1$-$C_{20}$ alkoxide, aryloxide, $C_3$-$C_{20}$ alkyldiketonate, aryldiketonate, $C_1$-$C_{20}$ carboxylate, arylsulfonate, $C_1$-$C_{20}$ alkylsulfonate, $C_1$-$C_{20}$ alkylthio, arylthio, $C_1$-$C_{20}$ alkylsulfonyl, and $C_1$-$C_{20}$ alkylsulfinyl, wherein the moiety is substituted or unsubstituted.

7. The method of claim 1 wherein the catalyst is of the formula:

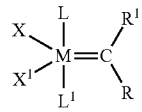

wherein:
M is ruthenium or osmium;
X and $X^1$ are either the same or different and are any anionic ligand;
L and $L^1$ are either the same or different and are any neutral electron donor;
R and $R^1$ are either the same or different and are each independently hydrogen or a substituent selected from the group consisting of $C_1$-$C_{20}$ alkyl, $C_2$-$C_{20}$ alkenyl, $C_2$-$C_{20}$ alkynyl, aryl, $C_1$-$C_{20}$ carboxylate, $C_1$-$C_{20}$ alkoxy, $C_2$-$C_{20}$ alkenyloxy, $C_2$-$C_{20}$ alkynyloxy, aryloxy, $C_2$-$C_{20}$ alkoxycarbonyl, $C_1$-$C_{20}$ alkylthio, $C_1$-$C_{20}$ alkylsulfonyl and $C_1$-$C_{20}$ alkylsulfinyl, wherein each of the substituents is substituted or unsubstituted.

8. The method of claim 1 wherein the at least one compatibilizing functionality is an isocyanate group.

9. A method for adhering a polyolefin resin to a substrate surface comprising:
    contacting a polyolefin resin with an adhesion agent in the presence of a metal carbene metathesis catalyst to form a resin/agent mixture, the adhesion agent comprising at least one $C_3$-$C_{200}$ olefin compound having at least one metathesis active double bond, wherein the olefin is substituted or unsubstituted, and at least one compatibilizing functionality for interacting with the substrate surface; and
    applying the mixture to the substrate surface; wherein the polyolefin resin is substituted with a moiety selected from the group consisting of thiol, thioether, ketone, aldehyde, ester, ether, amine, amide, nitro, carboxylic acid, disulfide, carbonate, isocyanate, carboiimide, carboalkoxy, carbamate, halogen, and pseudohalogen.

10. The method of claim 9 wherein the substrate surface comprises amino functional groups.

11. The method of claim 10 wherein the substrate surface comprises organic hydroxyl groups.

12. The method of claim 9 wherein the polyolefin resin is prepared from one or more monomers selected from the group consisting of cyclopropenes, cyclobutenes, benzocyclobutenes, cyclopentenes, cyclopentadiene oligomers, cyclohexenes, cycloheptenes, cyclooctenes, cycooctadienes, norbornenes, norbornadienes, [2.2.1] bicycloheptenes, [2.2.2] bicyclooctenes, cyclohexenylnorbornenes, and norbornene dicarboxylic anhydrides.

13. The method of claim 9 wherein the polyolefin resin is prepared via a ring opening metathesis polymerization of a cyclic olefin.

14. The method of claim 9 wherein the polyolefin resin is poly-DCPD.

15. The method of claim 9 wherein the catalyst is of the formula:

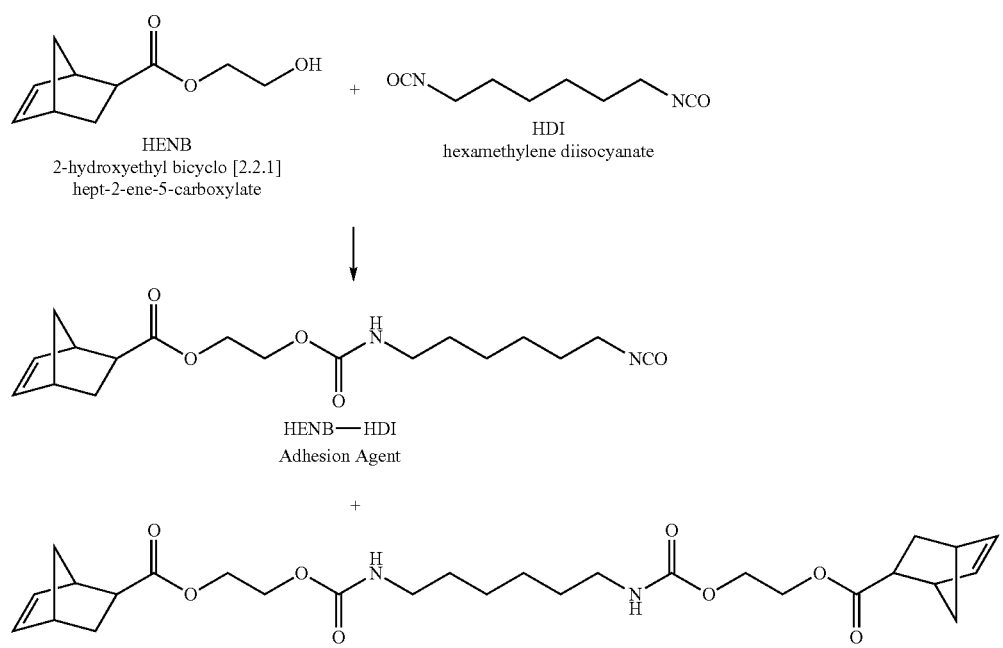

wherein:
M is ruthenium or osmium;
X and $X^1$ are either the same or different and are any anionic ligand;
L and $L^1$ are either the same or different and are any neutral electron donor;
R and $R^1$ are either the same or different and are each independently hydrogen or a substituent selected from the group consisting of $C_1$-$C_{20}$ alkyl, $C_2$-$C_{20}$ alkenyl, $C_2$-$C_{20}$ alkynyl, aryl, $C_1$-$C_{20}$ carboxylate, $C_1$-$C_{20}$ alkoxy, $C_2$-$C_{20}$ alkenyloxy, $C_2$-$C_{20}$ alkynyloxy, aryloxy, $C_2$-$C_{20}$ alkoxycarbonyl, $C_1$-$C_{20}$ alkylthio, $C_1$-$C_{20}$ alkylsulfonyl and $C_1$-$C_{20}$ alkylsulfinyl, wherein each of the substituents is substituted or unsubstituted.

16. The method of claim 9 wherein the at least one compatibilizing functionality is an isocyanate group.

* * * * *